United States Patent [19]

Wolfram et al.

[11] Patent Number: 4,601,299

[45] Date of Patent: Jul. 22, 1986

[54] HAIR SETTING PROCESS AND TISSUE

[75] Inventors: Leszek J. Wolfram, Stamford; Linda Albrecht, W. Redding, both of Conn.

[73] Assignee: Clairol Incorporated, New York, N.Y.

[21] Appl. No.: 562,681

[22] Filed: Dec. 19, 1983

[51] Int. Cl.$^4$ .............................................. A45D 7/00
[52] U.S. Cl. ...................................................... 132/7
[58] Field of Search ............................. 132/7, 33 R, 9

[56] References Cited

U.S. PATENT DOCUMENTS

| | | | |
|---|---|---|---|
| 1,894,431 | 1/1933 | Vaghelatos | 132/33 R |
| 2,028,051 | 1/1936 | Durham et al. | 132/33 R |
| 3,367,345 | 2/1968 | Riley | 132/7 |

OTHER PUBLICATIONS

Sagarin, Cosmetics Science and Technology, 1957, pp. 532,572-573,709,608,569.

Primary Examiner—Gregory E. McNeill
Attorney, Agent, or Firm—Gabriel P. Katona

[57] ABSTRACT

The invention concerns a process wherein a premoistened tissue is applied to the ends of a strand of hair, the strand is wound around a preheated curler and left thereon until substantially dry. The tissue is saturated with an aqueous solution which may contain the water solvent alone, or also dissolved in the water a hair conditioner and/or a setting lotion.

21 Claims, No Drawings

HAIR SETTING PROCESS AND TISSUE

The present invention relates to a process for setting hair, more particularly the present invention relates to a process for imparting longer lasting curls through the use of heated implements.

BACKGROUND OF THE INVENTION

Imparting a wave to hair generally involves rendering the hair pliable, imparting the curl, such as by winding it around a curler before or after it was rendered pliable, and then removing the pliability whereby the hair becomes set in its curled shape. Two general techniques are currently used to impart a change in hair configuration. The first is referred to as permanent (cold) waving. This involves winding the wet hair around so-called waving rods and subjecting the wound up hair to a chemical which cleaves the disulfide bonds. After the desired hair configuration has been achieved, thus completing this process, another chemical is employed to reestablish the disulfide bonds or other cross-links. The resultant wave (or curl) is not removed by shampooing or other cosmetic treatments such as hair coloring or bleaching.

The second technique is referred to as temporary or cohesive setting of hair. In contrast to permanent waving which involves chemical modification of hair, temporary setting manipulates only the moisture content of the hair to attain changes in fiber geometry. This can be readily accomplished either by wetting the hair, winding it on curlers or rollers and allowing it to dry, or alternatively, by employing heated rollers or curling irons as setting implements with dry hair. The set attained in this way, while somewhat stable to ambient humidity is lost completely on wetting or shampooing.

In the case of hair setting employing heat, it has been found that slight amounts of water will improve the pliability of hair and thus improve the quality and lasting of the curl. There is a critical threshold of the quantity of added water and exceeding that threshold produces no additional benefits and indeed, may result in set deterioration. It is also desirable to minimize the amount of water employed because any excess water would have to be driven out of the hair before it can be removed from the curler or the curling iron, since only dry hair will maintain a satisfactory curl. Moist hair, or hair exposed to considerable humidity, will loose a water-wave curl rather rapidly.

BRIEF DESCRIPTION OF THE INVENTION

The present invention relates to a process for imparting a wave to hair which comprises applying a premoistened webbing to the ends of a small section of dry hair, winding the hair around a preheated roller, and then removing the hair from the roller and the webbing from the hair. The webbing is suitably a paper-thin fabric, for example of nonwoven rayon, which is premoistened suitably with water or with an aqueous emulsion or solution of water soluble or emulsifiable conditioning agent. The water can contain in solution optionally a further, slight amount of water soluble setting agent.

The invention also relates to a webbing for wrapping the ends of the hair, said webbing being impregnated with water and optionally a conditioning agent and a setting agent dissolved or emulsified in the water.

SUMMARY DESCRIPTION OF THE PRIOR ART

A great deal of prior art is available, describing premoistened or pretreated webbings, such as of paper, for various uses in connection with hair. Some of these webbings are supposed to condition or impart other properties to hair such as U.S. Pat. Nos. 3,954,113; 4,149,551; 4,206,195 and 4,206,196 and European patent application No. 47,116.

A number of patents disclose premoistened webbings used in currently no longer employed permanent waving, by wrapping the webbing over the exterior of a wound up wet strand of hair, such as in U.S. Pat. Nos. 1,712,489; 1,531,291; 1,440,163; and 2,314,392.

There is also disclosed in U.S. Pat. No. 171,885 the use of a dry nonabsorbent end paper in permanent waving.

Also known are pretreated paper tissues for a variety of purposes, such as for facial antibacterial sanitization (U.S. Pat. No. 3,138,533), germicidal tissue to wipe surfaces germ-free (U.S. Pat. No. 3,227,614) and the like.

DETAILED DESCRIPTION OF THE INVENTION

In referring to "rollers" or to "curlers", each word is intended to be used synonymously with the other, and it is also intended to encompass by the use of these words equivalent other devices such as curling irons of the type which are employed in to produce curls in hair.

The premoistened webbing or tissues of the present invention are employed in a setting process which, by definition, is used in connection with dry or substantially dry hair. As the webbing or tissue is applied to the end of the hair, it can be conveniently folded over a small section of hair which is then wound over a preheated roller or curling iron. In this manner the premoistened webbing which enwraps the hair, directly contacts the surface of the preheated roller. The remaining length of hair is wound onto the curler and the premoistened webbing is now located within the would up section of hair. The heat of the preheated curler or curling iron evaporates the water and any other volatile ingredients that assist to enhance the curl. As driven from the interior of the hair by means of the heated roller or curling iron, the water and other vapors penetrate through the individual hair fibers thereby making them more pliable and thus conforming better to the desired geometrical configuration.

The continued conveyance of heat from the interior of the wound up hair dries out the tissue and eventually also removes all water from the surface of the hair, at which point the hair can be unwound from the roller and the setting is completed. In addition to the process of imparting curls (or a wave) to hair, the present invention also includes novel impregnated webbings or tissues which contain the desired other impregnating agent as described below.

The webbing can be of woven or nonwoven fibrous material, including paper. The words "webbing" and "tissue" are used entirely interchangeably herein. The size and shape of the webbing are not critical, and can be optimized by routine experimentation in considering such factors as absorbency, size and shape of curlers, and the like. Any suitable moisture-retaining dispenser can be employed for the premoistened tissues in accordance with the present invention.

From about 0.1 to about 1 gram of water can be contained in each tissue, however, suitably not more than from about 0.3 to about 0.6 grams of water is used per tissue because the use of more water will usually not bring about increased benefits. Water soluble conditioning agents are usually cationic compounds such as surfactants and quaternary ammonium compounds, or even cationic polymers. Typical of such materials are stearalkonium chloride. The following additional exemplary illustrations of conditioning agents are listed by their CTFA names (as given in the CTFA Cosmetic Ingredient Dictionary, Third Edition, published by The Cosmetic, Toiletry and Fragrance Association, Inc.):

Quaternium - 8
Quaternium - 18
Quaternium - 24
Quaternium - 52
Quaternium - 56 and
Quaternium - 70

Suitably from about 0.02% to about 2% by weight, of the conditioning agent can be employed in the composition.

Water emulsified conditioning products can also include silicones such as amodimethicone and its derivatives.

Setting resins which may assist in causing a lasting curl are generally water soluble materials that are compatible with the other conditioning ingredients, such as polyvinylpyrrolidone, polyvinyl alcohol, copolymer of vinyl acetate and vinylpyrrolidone, acrylate-acrylamide copolymer, vinyl acetatecrotonic acid copolymer, and the like.

Suitably from about 0.1% to about 4% by weight of setting agent can be contained in the composition.

In the following examples, nonwoven rayon fabric towelettes were impregnated with various compositions, in accordance with the present invention. The towelettes impregnated with each solution were applied similarly to the manner in which end-papers are applied to the rolling up of hair strands in permanent waving, by enveloping the ends of the hair within the towelette.

Three and one half inch square towelettes were used in the examples, each impregnated with an aqueous lotion load of 0.35 to 0.4 g. The lotion load was chosen to obtain a dry curl within 15 minutes on the heated roller.

The following compositions were employed, with water making up the balance to 100% (wt.):

EXAMPLE 1

0.2% steartriminium chloride
0.6% copolymer of vinyl acetate/crotonic acid

EXAMPLE 2

0.1% Arquad S-50

EXAMPLE 3

0.1% Arquad S-50
0.5% polyvinylpyrrolidone

EXAMPLE 4

0.2% stearalkonium chloride
1.0% polyvinylpyrrolidone

EXAMPLE 5

1.2% amodimethicone
1.0% polyvinylpyrrolidone

EXAMPLE 6

0.1% soytrimmonium chloride
1.0% copolymer of vinyl acetate/vinyl pyrrolidone

The curls produced showed vastly improved curl holding ability when the relaxation was measured as a function of time at constant temperature and humidity as compared to curls set without the premoistened towelettes.

Human test panels fully confirmed the results obtained using laboratory tresses. Thus, through the use of premoistened towelettes the following can be attained: a greater degree of curliness; a softer, silkier feel to the hair; reduction of static flyaway; more body and manageability and longer lasting curls.

We claim:

1. A process for imparting a wave to hair, which comprises applying a premoistened webbing to the end of a section of dry hair, winding the section of hair around a preheated roller, and then removing the hair from the roller and the webbing from the hair.

2. The process of claim 1, wherein the webbing is of woven or of nonwoven fibers.

3. The process of claim 1, wherein the webbing is paper.

4. The process of claim 2, wherein the webbing is premoistened with water.

5. The process of claim 1, wherein from about 0.1 to about 1 g. liquid is employed in the premoistened webbing.

6. The process of claim 5, wherein from about 0.3 to about 0.6 g. of liquid is employed in the premoistened webbing.

7. The process of claim 4 wherein the webbing is premoistened with an aqueous solution or emulsion of a water soluble or emulsifiable conditioning agent.

8. The process of claim 7, wherein the conditioning agent is a cationic polymer conditioner or an emulsified silicone conditioner.

9. The process of claim 6, wherein the cationic polymer is stearalkonium chloride, Quaternium -8, -18, -24, -52, -56 or -70, and the emulsified silicone is amodimethicone or a derivative thereof.

10. The process of claim 7, wherein the premoistening aqueous solution or emulsifier further comprises a water soluble setting agent which is compatible with said conditioning agent.

11. The process of claim 9, wherein said setting agent is present in a concentration of from about 0.1% to about 4.0% of the weight of the solution or emulsion.

12. The process of claim 9, wherein said setting agent is at least one of polyvinylpyrrolidone, polyvinyl alcohol, copolymer of vinyl acetate and vinylpyrrolidone, acrylate-acrylamide copolymer, and vinyl acetate-crotonic acid copolymer.

13. A premoistened webbing for improving the setting of hair, which comprises a webbing for wrapping the hair section, said webbing being impregnated with water.

14. The premoistened webbing of claim 13, wherein from about 0.1 to about 1 gram of water is contained in the webbing.

15. The premoistened webbing of claim 14, wherein from about 0.3 to about 0.6 grams of water is contained in the webbing.

16. The premoistened webbing of claim 15, wherein the webbing contains an aqueous solution or emulsion of a water soluble or emulsifiable conditioning agent.

17. The premoistened webbing of claim 16, wherein the conditioning agent is a cationic polymer conditioner or an emulsified silicone conditioner.

18. The premoistened webbing of claim 17, wherein the cationic polymer is stearalkonium chloride, Quaternium -8, -18, -24, -52, -56 or -70, and the emulsified silicone is amodimethicone or a derivative thereof.

19. The premoistened webbing of claim 16, further comprising a water soluble setting agent which is compatible with said conditioning agent.

20. The premoistened webbing of claim 19, wherein said setting agent is present in a concentration from about 0.1% to about 4.0% of the weight of the solution or emulsion.

21. The premoistened webbing of claim 19, wherein the said setting agent is at least one of polyvinylpyrrolidone, polyvinyl alcohol, copolymer of vinyl acetate and vinylpyrrolidone, acrylate-acrylamide copolymers, and vinyl acetate-crotonic acid copolymer.

* * * * *